United States Patent [19]

Narayanan et al.

[11] Patent Number: 6,024,972
[45] Date of Patent: Feb. 15, 2000

[54] WATER-FREE CONCENTRATE OF AMITRAZ INSECTICIDE AND CLEAR POUR-ON FORMULATIONS THEREOF

[75] Inventors: Kolazi S. Narayanan, Wayne, N.J.; Domingo Jon, New York, N.Y.; Donald Prettypaul, Englewood, N.J.

[73] Assignee: ISP Investments Inc., Wilmington, Del.

[21] Appl. No.: 09/121,072

[22] Filed: Jul. 21, 1998

[51] Int. Cl.$^7$ .............................. A01N 25/00; A61K 31/66
[52] U.S. Cl. ........................... 424/405; 424/406; 424/407; 504/116; 514/136; 514/255; 514/481; 514/521
[58] Field of Search ..................................... 424/405–407; 504/116; 514/136, 255, 481, 521

[56] References Cited

U.S. PATENT DOCUMENTS

| | | | |
|---|---|---|---|
| 4,438,137 | 3/1984 | Allan | 424/330 |
| 5,130,135 | 7/1992 | Van Tonder | 424/405 |
| 5,354,726 | 10/1994 | Narayanan et al. | 504/116 |

*Primary Examiner*—Bennett Celsa
*Attorney, Agent, or Firm*—Walter Katz; William J. Davis; Marilyn J. Maue

[57] ABSTRACT

A water-free concentrate comprising, by weight, (a) 3–20% of amitraz insecticide, optionally with other agriculturally active chemicals, for example, a pyrethroid;

(b) 30–80% of a nonionic surfactant having an HLB <7, and (c) 5–30% of a $C_1$–$C_8$ alkyl pyrrolidone solvent.

Clear, pour-on formulations of about 5–60% by weight of the concentrate and 40–95% of an oil are described.

6 Claims, No Drawings

WATER-FREE CONCENTRATE OF AMITRAZ INSECTICIDE AND CLEAR POUR-ON FORMULATIONS THEREOF

BACKGROUND OF THE INVENTION

1. Field of the Invention

This invention relates to delivery systems for agriculturally active chemicals, and, more particularly, to water-free concentrates of amitraz insecticide, and to pour-on formulations of the concentrate and an oil which are clear and stable over an extended period of time.

2. Description of the Prior Art

Amitraz is a water-insoluble insecticide which is used extensively to control infestation of cattle, pigs and sheep. However, at present there is no available formulation for applying the insecticide directly to the animal in a convenient manner.

Accordingly, it is an object of this invention to provide a water-free concentrate of amitraz, and pour-on formulations thereof, which are clear, water-free and stable over an extended period of time.

SUMMARY OF THE INVENTION

What is described herein is a water-free concentrate comprising, by weight, (a) 3–20% of amitraz insecticide, optionally with other agriculturally active chemicals, preferably a pyrethroid, (b) 30–80% of a nonionic surfactant or surfactants having an HLB <7, and (c) 5–30% of a $C_1$–$C_8$ alkyl pyrrolidone solvent, preferably N-methyl pyrrolidone or N-octyl pyrrolidone, or mixtures thereof.

Preferably, the concentrate comprises (a) 10–15%, (b) 65–75%, HLB <5 and (c) 10–20%; and is stored over a molecular sieve or in the presence of an additive such as Stabaxol-I (2,2',6,6'-tetraisopropyldiphenyl carbodiimide).

Use formulations of the concentrate are prepared as clear, water-free, pour-on solutions comprising, by weight, 5–60% of the concentrate and 70–95% of an oil, such as a hydrocarbon oil, e.g. petroleum oil, or a mineral or vegetable oil. Such formulations also are preferably stored over molecular sieve which is present in an amount of about 1–10% by weight of the formulation.

DETAILED DESCRIPTION OF THE INVENTION

In this invention, amitraz insecticide is formulated into an oil-based, pour-on composition containing a high loading of the active in a matrix of an oil such as vegetable oil or petroleum oil as the medium, and an N-$C_1$–$C_8$ alkyl pyrrolidone for solubilization, stability and spreading.

Other agricultural active chemicals which may be admixed with Amitraz herein include the following: permethrin; permethrin+Kathon; D-allethrin; tetramethrin; deltamethrin; piperonyl butoxide; mixed pyrethroids; dicofol; tefluthrin; resmethrin; phenothrin; kadethrin; bifenthrin; cyhalothrin; cycloprothrin; tralomethrin; cyfluthrin; fenvalerate and isomers; fenpropathrin; fluvalenate; rotenone; biphenyl compounds like, methoxychlor; chlorbenzilate; bromopropylate; and chlorfenethol. Pyrethroids are preferred.

The invention will be described further with reference to the following examples, in which: Alkamuls® STO=Sorbitan trioleate Alkamuls® SMO=Sorbitan monooleate Alkamuls® CO-15=Castor oil ethoxylate (15EO) Agsol® EX 1=N-methylpyrrolidone (ISP) Agsol® EX 8=N-octylpyrrolidone (ISP) Agrimer® VEMA ES 42=Gantrez® ES 425 (ISP) Orchex® 796=Petroleum process oil (Exxon) Molecular sieve=Molecular sieve 4A Stabaxol-I®=2,2',6,6'-tetraisopropyldiphenyl carbodiimide (Rhein-Chemie).

EXAMPLE 1

An oil based formulation of amitraz as the active ingredient was prepared by dissolving 2.78 g of technical amitraz grade (72% a.i.) in 97.22 g of a matrix formulation of 2.72 g of N-methylpyrrolidone, sold as Agsol® EX 1, and 11.7 g of sorbitan monooleate, sold as Alkamuls® SMO; and diluted with 82.8 g of soy bean oil. 5 g of a molecular sieve 4A was added to the matrix formulation before dissolution of the amitraz. The resultant formulation remained stable and clear at room temperature for more than 14 days.

EXAMPLE 2

Another oil based formulation with amitraz as the active ingredient was prepared by dissolving 3.3 g of technical amitraz grade (72% a.i.) in 96.7 g of a matrix formulation of 2.7 g of N-methylpyrrolidone and 14 g of Alkamuls® SMO, and diluted with 80 g of soy bean oil. The matrix formulation was pretreated with 5 g of a molecular sieve 4A before adding the amitraz. The resulting formulation also remained stable and clear when kept at room temperature for more than 14 days.

EXAMPLE 3

Still another clear oil based formulation with amitraz as the active ingredient was prepared by dissolving 2.78 g of technical amitraz grade (72% a.i.) in 97.22 g of a matrix consisting of 2.72 g of N-methylpyrrolidone and 14.1 g of Alkamuls® SMO, and diluted with 80.4 g of soy bean oil. The matrix formulation was pretreated with the addition of 5 g of a molecular sieve 4A before adding the amitraz. This formulation remained stable for greater than 14 days at room temperature.

EXAMPLE 4

As above, an oil based formulation with amitraz as the active ingredient was prepared by dissolving 2.8 g of technical amitraz grade (72% a.i.) pretreated with 7 g molecular sieve 4A in 97.2 g of a matrix formulation of 2.7 g of N-methylpyrrolidone and 12.6 g of Alkamuls® SMO, and diluted with 81.8 g of soy bean oil. This formulation remained physically stable and clear when kept at room temperature for more than two weeks.

EXAMPLE 5

A clear oil based concentrate formulation with amitraz as the active ingredient was prepared by dissolving 14 g of technical amitraz grade (72% a.i.) in 86 g of a concentrate matrix of 7.5 g of N-octyl-pyrrolidone, sold as Agsol® EX 8, 30 g of Alkamuls® STO and 48.5 g of Orchex® 796. The concentrate was clear for at least the 2 weeks of observation. The concentrate then was further diluted at the ratio of 1:5 with soy bean oil. The resulting formulation contained 2.8 g of amitraz technical. The formulation remained stable for greater than 14 days at room temperature. HPLC analysis showed greater than 75% retention of a.i. after storing the sample at 52° C. for 6 days. After 14 days a retention of 60% was observed.

EXAMPLE 6

A clear oil based formulation with amitraz as the active ingredient was prepared by dissolving 2.8 g of technical amitraz grade (72% a.i.) in 97.8 g of a matrix formulation of 1 g of N-octylpyrrolidone, 8 g of Alkamuls® STO and diluted with 88.2 g of Orchex® 796. This formulation remained stable for at least 5 days when kept at room temperature. A HPLC analysis showed a 60% retention of a.i. after storing for 27 days.

EXAMPLE 7

A clear oil based concentrate formulation with amitraz as the active ingredient was prepared by dissolving 14 g of technical amitraz grade (72% a.i.) in 86 g of a concentrate matrix of 7.5 g of N-octyl-pyrrolidone and 22.5 g of Alkamuls® STO and 56 g of Orchex® 796. The concentrate was clear during 2 weeks of observation. The concentrate was further diluted at the ratio of 1:5 with soy bean oil to provide a formulation with 2.8 g of amitraz technical. This formulation remained stable for greater than 14 days at room temperature.

EXAMPLE 8

An oil based formulation with amitraz as the active ingredient was prepared by dissolving 2.8 g of technical amitraz grade (72% a.i.) in 97.2 g of a matrix formulation of 2.7 g of N-methylpyrrolidone and 12.6 g of Alkamuls® STO, and diluted with 81.8 g of soy bean oil. This formulation remained physically stable and clear when kept at room temperature for more than two weeks. The matrix formulation was pretreated with the addition of 9 g of a molecular sieve before adding the amitraz. HPLC analysis showed greater than 75% retention of a.i. after storing the sample at 52° C. for 14 days. In the absence of a molecular sieve, the active degraded completely when stored for a similar time interval.

EXAMPLE 9

A series of formulated compositions containing 0.14 g of amitraz (72% active) was prepared with 2.8 g of N-methylpyrrolidone, 97.2 g of a mixture of soy bean oil and Alkamuls® SMO. The formulations are given in Table 1 below. Compositions containing at least 12 g of Alkamuls SMO were clear and stable for at least 2 weeks, while compositions containing 10 g or less of Alkamuls SMO showed some precipitate formation after 2 weeks. In all samples tested, amitraz was stabilized by addition of 5 g of a molecular sieve 4A added to the clear formulation.

TABLE 1

| Percentage | | | | | | | | | | |
|---|---|---|---|---|---|---|---|---|---|---|
| Amitraz (72% active) | 0.14 | 0.14 | 0.14 | 0.14 | 0.14 | 0.14 | 0.14 | 0.14 | 0.14 | 0.14 |
| Agsol EX 1 | 2.8 | 2.8 | 2.8 | 2.8 | 2.8 | 2.8 | 2.8 | 2.8 | 2.8 | 2.8 |
| Soy bean oil | 82.7 | 84.2 | 85.2 | 87.2 | 88.2 | 89.2 | 90.2 | 91.2 | 92.2 | 93.2 |
| Alkamuls SMO | 14.5 | 13.0 | 12.0 | 10.0 | 9.0 | 8.0 | 7.0 | 6.0 | 5.0 | 4.0 |
| Observation | | | | | | | | | | |
| 2 weeks | clear | clear | clear | ppt | ppt | ppt | ppt | ppt | ppt | ppt |

EXAMPLE 10

A clear oil based formulation with amitraz as the active ingredient was prepared by dissolving 2.78 g of technical amitraz grade (72% a.i.) in 87.22 g of a matrix formulation of 2.44 g of N-methylpyrrolidone and 12.6 g of Alkamuls SMO, and diluted with 72.1 g of soy bean oil. 10 g of Stabaxol® I was added to the formulation. The formulation was stable for more than 2 weeks at 52° C. After 2 weeks at 52° C., a 99% recovery of amitraz was observed, as determined by HPLC analysis.

EXAMPLE 11

A clear oil based formulation with amitraz as the active ingredient was prepared by dissolving 2.8 g of technical amitraz grade (72% a.i.) in 88.2 g of a matrix formulation of 2.5 g of N-methylpyrrolidone and 12.7 g of Alkamuls SMO, and diluted with 73 g of soy bean oil. The matrix formulation was pretreated with the addition of 9 g of a molecular sieve 4A before adding the amitraz. After 2 weeks at 52° C., a 78% recovery of amitraz was obtained, as determined by HPLC analysis.

EXAMPLE 12

A clear oil based formulation with amitraz as the active ingredient was prepared by dissolving 14 g of technical amitraz grade (72% a.i.) and 1 g deltamethrin in 76 g of a concentrate matrix of 6.6 g of N-octyl-pyrrolidone, 19.9 g of Alkamuls® STO and 49.5 g of Orchex® 796. 10 g of Stabaxol® I was added to the formulation. The concentrate was clear during 2 weeks of observation. After 2 weeks at 52° C., an 80% recovery of both the amitraz and deltamethrin actives was obtained, as determined by HPLC analysis.

EXAMPLE 13

A clear oil based formulation was prepared by dissolving 2.8 g of technical amitraz grade (72% a.i.) and 0.6 g deltamethrin in 94.6 g of a matrix formulation of 2.6 g of N-methylpyrrolidone and 13.7 g of Alkamuls® SMO and diluted with 78 g of soy bean oil. 2 g of Stabaxol® I was added to the formulation. The formulation was stable and clear for more than 2 weeks at 52° C. After 2 weeks at 52° C., a greater than 80% recovery of both the amitraz and deltamethrin was obtained, as determined by HPLC analysis.

EXAMPLE 14

A clear oil based formulation with amitraz and deltamethrin as active ingredients was prepared by dissolving 14 g of technical amitraz grade (72% a.i.) and 1 g deltamethrin in 80 g of a concentrate matrix of 6.9 g of N-octylpyrrolidone, 20.9 g of Alkamuls® STO and 52.1 g of Orchex® 96. 5 g of Stabaxol® I was added to the formulation. The formulation was clear during 2 weeks of observation. After 2 weeks at 52° C., a greater than 85% recovery of both the amitraz and deltamethrin was obtained, as determined by HPLC analysis.

EXAMPLE 15

A clear oil based concentrate formulation with amitraz as the active ingredient was prepared by dissolving 14 g of technical amitraz grade (72% a.i.) in 76 g of a concentrate matrix consisting of 6.6 g of N-octylpyrrolidone, 19.9 g of Alkamuls® STO and 49.5 g of Orchex® 796. 10 g of Stabaxol® I was added to the formulation. The concentrate was clear during 2 weeks of observation. After 2 weeks at 52° C., <80% recovery of both amitraz and deltamethrin was obtained as determined by HPLC analysis.

While the invention has been described with particular reference to certain embodiments thereof, it will be understood that changes and modifications may be made which are within the skill of the art. Accordingly, it is intended to be bound only by the following claims.

What is claimed is:

1. A clear, water-free oil-based pour-on formulation comprising by weight (1) 5–60% of a concentrate of amitraz insecticide comprising:

(a) 3–20% of amitraz, optionally with other agriculturally active chemicals, (b) 30–80% of a nonionic surfactant or surfactants having an HLB of <7, and (c) 5–30% of a $C_1$–$C_8$ alkyl pyrrolidone solvent, and (2) 40–95% of an oil.

2. A formulation according to claim 1 wherein (a) is 5–15%, (b) is 65–75%, HLB <5 and (c) is 10–20%.

3. A formulation according to claim 1 wherein (a) is 12%, (b) is 70%, HLB is 4.3 and (c) is 13.5%.

4. A formulation according to claim 1 in which (c) is N-methylpyrrolidone or N-octylpyrrolidone, or mixtures thereof.

5. A formulation according to claim 1 in which (a) also includes a pyrethroid.

6. A formulation according to claim 1 in which the oil is a hydrocarbon, a mineral or a vegetable oil.

* * * * *